United States Patent [19]

Tanihara et al.

[11] Patent Number: 4,889,917
[45] Date of Patent: Dec. 26, 1989

[54] PEPTIDE

[75] Inventors: Masao Tanihara; Kiichiro Oka; Hideaki Yamada; Akira Kobayashi, all of Kurashiki; Toshihide Nakashima, Toyonaka; Yoshiaki Omura, Mitsu; Koichi Takakura, Nishinomiya, all of Japan

[73] Assignee: Agency of Industrial Science Technology, Ministry of International Trade & Industry, Tokyo, Japan

[21] Appl. No.: 265,550

[22] Filed: Nov. 1, 1988

[30] Foreign Application Priority Data

Nov. 25, 1987 [JP] Japan .................................. 62-295370

[51] Int. Cl.⁴ ............................ C07K 7/08; C07K 7/10
[52] U.S. Cl. ...................................... 530/324; 530/325; 530/326; 530/327
[58] Field of Search ................ 530/324, 325, 326, 327

[56] References Cited

U.S. PATENT DOCUMENTS 4,518,527  5/1985  Numa et al. ......................... 530/327
4,552,965  11/1985  Parsons ............................... 546/206

OTHER PUBLICATIONS

Nature, vol. 299, pp. 793–797 (1982).
Nature, vol. 299, pp. 793–797 (1982), "Primary Structure of α-Subunit Precursor of *Torpedo californica* Acetylcholine Receptor . . . ", Noda et al.
*Proceedings of the National Academy of Sciences of the U.S.*, vol. 84, pp. 3633–3637, (1987), "Profile of the Continuous Antigenic Regions on the extracellular part of the α Chain of an Acetylcholine Receptor", Mulac–Jericevic et al.
*Biochemical and Biophysical Research Communications*, vol. 135, pp. 82–89, (1986); "Localization of a Highly Immunogenic Region on the Acetylcholine Receptor α-Subunit" Souroujon et al.

*Primary Examiner*—Lester L. Lee
*Attorney, Agent, or Firm*—Oblon, Spivak, McClelland, Maier & Neustadt

[57] ABSTRACT

A peptide is disclosed which is represented by the formula:

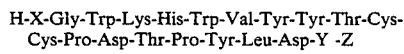

H-X-Gly-Trp-Lys-His-Trp-Val-Tyr-Tyr-Thr-Cys-
Cys-Pro-Asp-Thr-Pro-Tyr-Leu-Asp-Y -Z wherein one of X and Y stands for a single bond, an amino acid residue selected from the class consisting of Asp, Glu, Lys and a divalent group represented by the formula, (wherein n stands for an integer in the range of 1 to 17), or a peptide residue formed by peptide linkage of two to ten amino acid residues of at least one species selected from the class mentioned above, the other of X and Y stands for an amino acid residue selected from the class consisting of Asp, Glu, Lys and a divalent group represented by the formula, (wherein n stands for an integer in the range of 1 to 17), or a peptide residue formed by peptide linkage of two to ten amino acid residues of at least one species selected from the class mentioned above and Z stands for a hydroxyl group or an amino group, and two cysteinyl mercapto groups in the Cys-Cys moiety may be interlinked to each other to form a disulfide bond.

3 Claims, No Drawings

PEPTIDE

BACKGROUND OF THE INVENTION

1. Field of the Invention

This invention relates to a novel peptide.

The peptide provided by this invention is easily immobilized on a carrier and enabled to effect specific adsorption of a human antibody to a nicotinic acetylcholine receptor. The peptide of this invention is therefore useful for the therapy of myasthenia gravis which is held to have its main symptoms in the disorder caused in neuromuscular transmission by the autoantibody to the nicotinic acetylcholine receptor present on the postsynaptic membrane in the neuromuscular junctions

2. Prior Art Statement

It is reported in "Nature", vol. 299, pages 793-797 (1982) that the α-subunit precursor of the nicotinic acetylcholine receptor obtained from the electric organ of *Torpedo californica*, one species of electric ray, is composed of 461 amino acids and that the primary structure of the precursor has been successfully elucidated. According to this report, the amino acid sequence at the 183rd to 200th positions in the primary structure of the α-subunit precursor is represented by the formula -Gly-Trp-Lys-His-Trp-Val-Tyr-Tyr-Thr-Cys-Cys-Pro-Asp-Thr-Pro-Tyr-Leu-Asp-. In Proceedings of the National Academy of Sciences of the United States of America, Vol. 84, pages 3633-3637 (1987), it is reported that a peptide corresponding to the amino acid sequence at the 182nd to 198th position in the primary structure of the α-subunit of the nicotinic acetylcholine receptor obtained from the electric organ of *Torpedo californica* has been synthesized and that an adsorbent formed by immobilizing this peptide on an agarose type carrier (CNBr-activated Sepharose CL-4B) has an ability to bind itself with a mouse antibody and a rabbit antibody to the nicotinic acetylcholine receptor. In Biochemical and Biophysical Research Communications, Vol. 135, pages 82-89 (1986), it is reported that the α-subunit of the nicotinic acetylcholine receptor obtained from *Torpedo californica*, on hydrolysis with a protease, produces a fragment possessing a molecular weight of 18 kilo-daltons and presumed to correspond to the amino acid sequence at the 153rd to 350th positions in the primary structure of the α-subunit and that this fragment has an ability to bind itself with α-bungarotoxin and a mouse monoclonal antibody against the ligand binding site of the nicotinic acetylcholine receptor.

For the therapy of myasthenia gravis it is desired to establish a method for effective removal of the human autoantibody to the nicotinic acetylcholine receptor which is thought to be the main cause of myasthenia gravis.

OBJECT AND SUMMARY OF THE INVENTION

An object of this invention is to provide a novel peptide useful for efficient production of an adsorbent capable of effectively adsorbing the human antibody to the nicotinic acetylcholine receptor.

This invention accomplishes the object mentioned above by providing a peptide represented by the formula:

H-X-Gly-Trp-Lys-His-Trp-Val-Tyr-Tyr-Thr-Cys-Cys-Pro-Asp-Thr-Pro-Tyr-Leu-Asp-Y-Z  (I)

wherein one of X and Y stands for a single bond, an amino acid residue selected from the class consisting of Asp, Glu, Lys and a divalent group represented by the formula, $$-NH(CH_2)_nC-\underset{O}{\overset{\|}{}}$$

(wherein stands for an integer in the range of 1 to 17), or a peptide residue formed by peptide linkage of two to ten amino acid residues of at least one species selected from the class mentioned above and the other of X and Y stands for an amino acid residue selected from the class consisting of Asp, Glu, Lys and a divalent group represented by the formula, $$-NH(CH_2)_nC-\underset{O}{\overset{\|}{}}$$

(wherein n stands for an integer in the range of 1 to 17), or a peptide residue formed by peptide linkage of two to ten amino acid residues of at least one species selected from the class mentioned above, and Z stands for one member selected from the class consisting of hydroxyl group and amino group.

Regarding the Cys-Cys moiety in the amino acid sequence mentioned above, two cysteinyl mercapto groups may be interlinked to each other to form a disulfide bond.

DETAILED DESCRIPTION OF THE PREFERRED EMBODIMENTS

In this specification, various amino acid residues are denoted by conventional abbreviations. Many abbreviations are well known in the technical field to which the present invention pertains. Those used in this specification are enumerated below.

Asp: L-aspartic acid residue
Cys: L-cysteine acid residue
Glu: L-glutamic acid residue
Gly: Glycine residue
His: L-histidine residue
Leu: L-leucine residue
Lys: L-lysine residue
Pro: L-proline residue
Thr: L-threonine residue
Trp: L-tryptophane residue
Tyr: L-tyrosine residue
Val: L-valine residue Further in this specification, the description of amino acid sequence follows the convention that the amino acid at the N terminal is positioned on the lefthand side and the amino acid at the C terminal on the righthand side.

The symbols X and Y in the general formula (I) have the meanings defined above. Peptides having single bonds for both X and Y and peptides having an amino acid residue or a peptide residue deviating from the respective definition for either of X and Y have the possibility of not merely eluding efficient immobilization on a carrier but also failing to manifest sufficiently an ability to adsorb the human antibody to the nicotinic acetylcholine receptor even when they are immobilized on a carrier. The following peptide residues may be mentioned as concrete examples of the peptide residues denoted by the symbols X and Y in the general formula (I).

$-Asp-Asp-$, $-Glu-Glu-$, $-Lys-Lys-$, $-Gly-Gly-$, $-\!\!\!+NH(CH_2)_{11}\underset{\overset{\|}{O}}{C}+\!\!\!-_2$, $-\!\!\!+NH(CH_2)_{17}\underset{\overset{\|}{O}}{C}+\!\!\!-_2$, $-Asp-Glu-$, $-Asp-Gly-$, $-Glu-Asp-$, $-Glu-Lys-$, $-Lys-Glu-$, $-Lys-NH(CH_2)_{11}\underset{\overset{\|}{O}}{C}-$, $-Gly-Asp-$, $-Gly-Lys-$, $-NH(CH_2)_{11}\underset{\overset{\|}{O}}{C}-Glu-$, $-NH(CH_2)_{11}\underset{\overset{\|}{O}}{C}-Lys-$, $-NH(CH_2)_{17}\underset{\overset{\|}{O}}{C}-Asp-$, $-NH(CH_2)_{17}\underset{\overset{\|}{O}}{C}-Lys-$, $-Lys-Lys-Gly-$, $-\!\!\!+Asp+\!\!\!-_5$, $-\!\!\!+Glu+\!\!\!-_5$, $-\!\!\!+Lys+\!\!\!-_5$, $-\!\!\!+Gly+\!\!\!-_5$, $-\!\!\!+NH(CH_2)_{11}\underset{\overset{\|}{O}}{C}+\!\!\!-_5$, $-\!\!\!+NH(CH_2)_{17}\underset{\overset{\|}{O}}{C}+\!\!\!-_5$, $-Lys-Asp-Glu-Gly-NH(CH_2)_{17}\underset{\overset{\|}{O}}{C}-$, $-Gly-Lys-Glu-Glu-Asp-$, $-Asp-Glu-NH(CH_2)_{17}\underset{\overset{\|}{O}}{C}-Lys-Gly-Lys-$, $-\!\!\!+Asp+\!\!\!-_{10}$, $-\!\!\!+Glu+\!\!\!-_{10}$, $-\!\!\!+Lys+\!\!\!-_{10}$, $-\!\!\!+Gly+\!\!\!-_{10}$, $-\!\!\!+NH(CH_2)_{11}\underset{\overset{\|}{O}}{C}+\!\!\!-_{10}$, $-\!\!\!+NH(CH_2)_{17}\underset{\overset{\|}{O}}{C}+\!\!\!-_{10}$, $-Lys-Glu-Gly-NH(CH_2)_{11}\underset{\overset{\|}{O}}{C}-Asp-Asp-Lys-$ $-Lys-Glu-Gly-$, $-Lys-Glu-Glu-$ $-Gly-Asp-Asp-Lys-Lys-Gly-Gly-$ The synthesis of a peptide represented by the general formula (I) can be accomplished by any of the methods generally employed heretofore for the synthesis of peptides. As examples of such conventional methods, the solid-phase synthesis method and such liquid-phase synthesis methods as the stepwise elongation method and the fragment condensation method may be mentioned. From the operational point of view, it is convenient to effect the synthesis by the solid-phase method [as reported in Journal of the American Chemical Society, vol. 85, pages 2149–2154 (1963)].

Now, the manufacture of a peptide represented by the general formula (I) in accordance with the solid-phase method will be described below. This synthesis is accomplished by sequentially repeating an operation of binding through condensation to such a polymer insoluble in a reaction solvent as a styrene-divinylbenzene copolymer having bonded thereto an acyloxy group or an acylamino group obtained by removing a hydrogen atom respectively from an α-carboxyl group or an α-cabamoyl group possessed by an amino acid or an amino acid amide corresponding to the C terminal of the peptide aimed at the corresponding component amino acids in the order of their occurrence in the direction of the N terminal of the peptide, with such a functional group as α-amino group other than the α-carboxyl group possessed by the relevant amino acid kept in a protected form, and an operation of removing a protective group from the amino group to be caused to form the peptide bond such as the α-amino group, which group is possessed by the bound amino acid, thereby attaining gradual growth of a peptide chain and eventually completing a peptide chain corresponding to the peptide aimed at, and separating the peptide chain from the polymer and, at the same time, removing the protecting groups from the protected functional groups and consequently obtaining the peptide, and finally purifying the peptide. In this case, for the sake of precluding otherwise possible occurrence of side reactions, the separation of the peptide chain from the polymer and the removal of the protecting groups are desired to be simultaneously effected by the use of hydrogen fluoride. The purification of the peptide so obtained can be effectively attained by reverse-phase liquid chromatography.

Any of the peptides represented by the general formula (I) can be efficiently immobilized on a carrier. The peptide of the general formula (I) which is immobilized on a carrier manifests an ability to adsorb the human antibody to the nicotinic acetylcholine receptor in the body fluid such as serum, and does so-particularly conspicuously when it is subjected to a heat treatment. The carrier to be used in the immobilization of the peptide of the general formula (I) is desired to possess a hydrophilic surface and also possess a reactive functional group such as amino group, carboxyl group, or hydroxyl group available for the formation of a covalent bond with the peptide. When the peptide is to be used as an adsorbent for the adsorption of the human antibody to the nicotinic acetylcholine receptor in a body fluid, the carrier is further desired to be insoluble in the body fluid and to be porous. The porous carrier is advantageous in the respect that it has a large surface area available for the adsorption of the human antibody to the nicotinic acetylcholine receptor. To be used advantageously, this carrier is desired to possess an exclusive limiting protein molecular weight approximately in the range of $10^6$ to $10^9$ or an average pore diameter approximately in the range of 50 to 1,000 nanometers. The carrier can be used in a form freely selected from such forms as particulate form, fibrous form, sheet form, and hollow fiber form. As concrete examples of the carrier, cellulose type carriers represented by CM-cellulofine CH (a product possessing an exclusive limiting protein molecular weight of about $3\times10^6$, marketed by Seikagaku Kogyo Co., Ltd.), polyvinyl alcohol type carriers represented by CM-Toyopearl 650 C (a product possessing an exclusive limiting protein molecular weight of about $5\times10^6$, marketed by Toso K.K.), polyacrylamide type carriers represented by CM-Trisacryl M (a product possessing an exclusive limiting protein molecular weight of $1\times10^7$, marketed by Pharmacia-LKB, Sweden), agarose type carriers represented by Sepharose CL-4B (a product possessing an exclusive limiting protein molecular weight of $2\times10^7$, marketed by Pharmacia-LKB, Sweden), and other similar organic carriers, and porous glass represented by CPG-10-1000 (a product possessing an exclusive limiting molecular weight of $1 \times 10^8$ and an average pore diameter of 100 nm, marketed by Electro-nucleonics Corp., U.S.A.) and other similar inorganic carriers may be cited.

The immobilization of the peptide of the general formula (I) on the carrier is carried out by the methods generally employed heretofore in immobilizing peptides and proteins on a carrier. As examples of the such methods, there can be mentioned a method which effects the immobilization by converting the carboxyl group possessed by a carrier through the reaction thereof with N-hydroxysuccinimide into a succinimidoxycarbonyl group and causing the peptide of the general formula (I) to react in the portion of the amino group thereof with the succinimidoxycarbonyl group (activated ester method), a method which attains the immobilization by allowing the amino group or the carboxyl group possessed by a carrier to undergo a condensation reaction with the carboxyl group or the amino group of the peptide of the general formula (I) in the presence of a condensation reagent such as dicyclohexylcarbodiimide (condensation method), and a method which accomplishes the immobilization by crosslinking a carrier with the peptide of the general formula (I) by the use of such a compound as glutaraldehyde which possesses at least two functional groups (carrier crosslinking method). The adsorbent which is obtained by immobilizing the peptide of the general formula (I) on a carrier by the activated ester method possesses the highest ability to adsorb the human antibody to the nicotinic acetylcholine receptor. In order for the produced adsorbent to be capable of adsorbing a significant amount of the human antibody to the nicotinic acetylcholine receptor, the amount of the peptide of the general formula (I) to be immobilized on the carrier is generally required to be at least about $3 \times 10^{-8}$ mol/g (carrier). For the peptide of the general formula (I) thus immobilized on the carrier to be effectively utilized for the adsorption of the human antibody, the amount of peptide to be immobilized is desired to fall approximately in the range of $1 \times 10^{-7}$ to $2 \times 10^{-6}$ mol/g (carrier).

The peptide of the general formula (I) immobilized on the carrier is enable, in its unmodified form, of manifesting the ability to adsorb the human antibody to the nicotinic acetylcholine receptor. When it is subjected to the heat treatment as mentioned above, it is enabled to manifest this ability more conspicuously. This heat treatment is desired to be carried out at a temperature of at least 60° C. If the temperature of the heat treatment is unduly high, there may arise the possibility that the peptide and/or the carrier will be decomposed. Thus, it is desired to be kept from exceeding 180° C. The time of this heat treatment is desired to be at least about 5 minutes. If this time is unduly long, there is a possibility that the peptide and/or the carrier will be decomposed. Thus, it is desired not to exceed about one hour. Optionally, the heat treatment can be executed by heating the peptide immobilized on the carrier in water or an aqueous solution under the conditions specified above. For the sake of curbing the otherwise possible decomposition of the peptide, the heat treatment is desired to be carried out in a buffer solution such as a sodium chloride-containing phosphate buffer.

Now, the present invention will be described specifically below with reference to working examples. It should be noted, however, that this invention is not restricted by these examples.

EXAMPLE 1 represented by the formula,

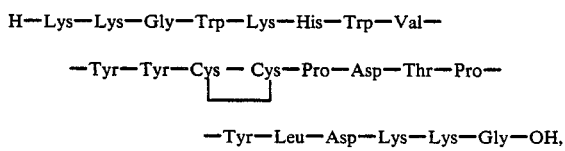

was synthesized by the solid-phase method using an automatic peptide synthesizing apparatus (produced by Applied Biosystems Inc., U.S.A. and marketed as "Model 430A"). In accordance with the series of operations indicated in Table 1, the amino acids selected from among L-aspartic acid, L-cysteine, glycine, L-histidine, L-leucine, L-lysine, L-proline, L-threonine, L-tryptophane, L-thyrosine, and L-valine corresponding to the component amino acids of the peptide in the order of occurrence in the direction of the N terminal of the peptide were sequentially bound to 0.64 g of a particulate resin of a styrene-divinylbenzene copolymer (the molar ratio of styrene to divinylbenzene 99:1) possessing a 4[N-(t-butoxycarbonyl)-glycyloxymethyl]-phenylacetamidomethyl group,

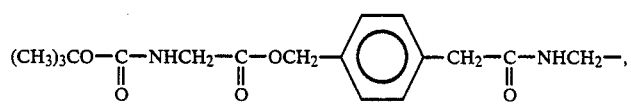

in a ratio of 0.78 m.mol/g (resin) (produced by Applied Biosystems Inc., U.S.A. and marketed under the tradename "PAM Glycine, t-Boc-Gly"). In the condensation reaction, the amino acids mentioned above were used respectively in the form of N-(t-butoxycarbonyl)-$O^4$-benzyl-L-aspartic anhydride, N-(t-butoxycarbonyl)-S-(p-methoxybenzyl)-L-cysteine anhydride, N-(t-butoxycarbonyl)glycine anhydride, $N^{\alpha}$-(t-butoxycarbonyl)-$N^{hu Im}$-tosyl-L-histidine anhydride, N-(t-butoxycarbonyl)-L-leucine anhydride, $N^2$-(t-butoxycarbonyl)-$N^6$-benzyloxycarbonyl-L-lysine anhydride, N-(t-butoxycarbonyl)-L-proline anhydride, N-(t-butoxycarbonyl)-$O^3$-benzyl-L-threonine anhydride, $N^{\alpha}$-(t-butoxycarbonyl)-L-triptophane anhydride, N-(t-butoxycarbonyl)-$O^4$-benzyl-L-thyrosine anhydride, and N-(t-butoxycarbonyl)-L-valine anhydride each in an amount of about 2 mols per mol of the substrate. The condensation reaction was carried out at normal room temperature. The reaction time was varied with the kind of amino acid to be condensed within the range of 18 to 30 minutes. Since the particular condensation reaction using the $N^{60}$-(t-butoxycarbonyl)-$N^{Im}$-tosyl-L-histidine anhydride did not show sufficient conversion, it was carried out a second time by repeating the steps 4 to 6 indicated in Table 1 after the series of operation indicated in Table 1 had been completed.

TABLE 1

| Step | Solvent and/or reagent used | Time (min.) | Number of rounds |
| --- | --- | --- | --- |
| 1 Removal of t-butoxycarbonyl group | Dichloromethane solution containing 33% by volume of trifluoroacetic acid (10 to 23 ml) | 1.3 | 1 |
| | Dichloromethane solution containing 50% by volume of trifluoroacetic acid (6 to 16 ml) | 18.5 | 1 |
| 2 Washing | Dichloromethane | 1 | 3 |
| 3 Neutralization | Dimethylformamide solution containing 10% by volume of diisopropylethylamine | 1 | 2 |
| 4 Washing | Dimethylformamide | 1 | 5 |
| 5 Condensation reaction | Dimethylformamide solution containing amino acid (10 to 25 ml) | 18 to 30 | 1 |
| 6 Washing | Dichloromethane | 1 | 5 |

The resin obtained after completion of the reactional operation on all the amino acids was washed on a glass filter sequentially with diethyl ether, dichloromethane, and methanol and then vacuum dried. Consequently there was obtained 2.1 g of dry resin. In a reaction vessel made of polytrifluoromonochloroethylene (produced by Peptide Kenkyusho K.K. and marketed as "HF-Reaction Apparatus, Model I"), 1 g of the dry resin was mixed with 1.5 ml of anisole and 0.25 ml of ethylmethyl sulfide and the resultant mixture and 10 ml of hydrogen fluoride added thereto at a temperature of $-20°$ C. were stirred for 30 minutes at the same temperature and for another 30 minutes at a temperature of 0° C. The resultant reaction mixture was evaporated under a vacuum to expel hydrogen fluoride, anisole, and ethyl methyl sulfide. The residue of the evaporation was thoroughly washed with diethyl ether on a glass filter. The residue of the washing was extracted with 2N aqueous acetic acid solution. When the extract was freeze-dried, there was obtained 0.5 g of crude peptide.

When this crude peptide was purified by fractionating reverse-phase high-speed liquid chromatography [column - a column packed with octadecylated silica gel possessing a particle diameter of 5 μm (produced by Chemco K.K. and marketed under the tradename "Develosil ODS 10 mm $\phi \times 300$ mm"); mobile phase — a mixed solvent of acetonitrile and water (with the concentration of acetonitrile gradually varied from 20 vol% to 35 vol% over a period of 20 minutes) containing 0.05% by volume of trifluoroacetic acid], there was obtained 50 mg of the purified peptide aimed at.

When the purified peptide was subjected to analyzing reverse-phase high-speed liquid chromatography [column— a column packed with octadecylated silica gel possessing a particle diameter of 5 μm (produced by Toso K.K. and marketed as "TSK gel ODS-80TM 4 mm $\phi \times 150$ mm"); mobile phase— a mixed solvent of acetonitrile and water (with the concentration of acetonitrile gradually varied from 5 vol % to 50 vol % over a period of 30 minutes) containing 0.05% by volume of trifluoroacetic acid; flow rate—1 ml/min.; method of detection - absorbancy at a wavelength of 210 nm], a single sharp peak was observed at 9.2 min. By FAB (fast speed atomic bombardment) mass spectrometry, the purified peptide was found to possess a molecular weight of 2,814 (theoretical value 2,815.21). This purified peptide was hydrolyzed with hydrochloric acid and the resultant hydrolyzate was analyzed for amino acid composition. The results of this analysis were as shown below: (The parenthesized numerals indicate theoretical values.) Lysine—5.23 (5), glycine—1.94 (2), tryptophane—2.02 (2), histidine—0.98 (1), valine —0.92 (1), thyrosine—3.07 (3), threonine—2.07 (2), cystine—0.85 (1), proline—2.13 (2), aspartic acid 2.10 (2), and leucine—1.00 (1).

EXAMPLES 2 TO 16

The peptides indicated in Table 2 were obtained by carrying out solid-phase synthesis of peptide and purification in the same manner as in Example 1. As solid-phase resins, a particulate resin of a styrene-divinylbenzene copolymer (the molar ratio of styrene to divinylbenzene 99:1) possessing a 4-[N-(tbutoxycarbonyl)-glycyloxymethyl]phenylacetamidomethyl group in a ratio of 0.78 m.mol/g (resin) (produced by Applied Biosystems Inc., U.S.A. and marketed under the tradename "PAM Glycine,t-Boc-Gly") was used in Example 2 and Example 0; a particulate resin of a styrene-divinylbenzene copolymer (the molar ratio of styrene to divinylbenzene 9:1) possessing a 4-[N-(t-butoxycarbonyl)-$O^4$-benzyl-α-L-aspartyloxymethyl]-phenylacetamidomethyl group in a ratio of 0.78 m.mol/g (resin) [produced by Applied Biosystems Inc., U.S.A. and marketed under the tradename "PAM Aspartic Acid,t-Boc-L-Asp (OBzl)"]in Example 3, Example 5, Example 8 and Example 12; a particulate resin of a styrene-divinylbenzene copolymer (the molar ratio of styrene to divinylbenzene 99:1) possessing a 4-[N-(t-butoxycarbonyl)-$O^5$-benzyl-α-Lglutamyloxymethyl]-phenylacetamidomethyl group in a ratio of 0.78 m.mol/g (resin) [produced by Applied Biosystems Inc., U.S.A. and marketed under the tradename "PAM Glutamic Acid,t-Boc-L-Glu(OBzl)"]in Example 4 and Example 6; a particulate resin of a styrene-divinylbenzene copolymer (the molar ratio of styrene to divinylbenzene 99:1) possessing a 4-[$N^2$-(t-butoxycarbonyl)-$N^6$-(chlorobenzyloxycarbonyl)-L-lysyloxymethyl]-phenylacetamidomethyl group in a ratio of 0.78 m.mol/g (resin) [produced by Applied Biosystems Inc., U.S.A. and marketed under the tradename "PAM Lysine,t-Boc-L-Lys (ClZ)"]in Example 7, Example 9 and Example 11; and a particulate resin of a styrene-divinylbenzene copolymer (the molar ratio of styrene to divinylbenzene 99:1) possessing an α-amino-p-methylbenzyl group in a ratio of 0.78 m.mol/g (resin) (produced by Applied Biosystems Inc., U.S.A. and marketed under the tradename "p-Methyl BHA Resin") in Examples 13 to 16. In the condensation reaction, L-glutamic acid, 12-aminododecanoic acid, and 18-aminooctadecanoic acid were used respectively in the form of N-(t-butoxycarbonyl)-$O^5$-benzyl-L-glutamic anhydride, 12-(t-butoxycarbonylamino)dodecanoic anhydride, and 18-(t-butoxycarbonylamino)octadecanoic anhydride.

In analyzing reverse-phase high-speed liquid chromatography, the produced peptides each showed a single peak. The molecular weights of the purified peptides determined by FAB mass spectrometry and the amino acid composition analyses of the products obtained by hydrolyzing the purified peptides with hydrochloric acid were as shown in Table 3.

TABLE 2

| Example | X | Y | Z |
|---|---|---|---|
| 2 | — | Gly | OH |
| 3 | —NH(CH$_2$)$_{17}$CO— | — | OH |
| 4 | —NH(CH$_2$)$_{11}$CO— | (—Glu—)$_5$ | OH |
| 5 | (—Lys—)$_5$ | (—Asp—)$_5$ | OH |
| 6 | (—Lys—)$_{10}$ | Glu | OH |
| 7 | (—Gly—)$_5$ | —Gly—Lys— | OH |
| 8 | —Lys—Asp—Glu—Gly—NH(CH$_2$)$_{17}$CO— | Asp | OH |
| 9 | Gly | —Lys—Lys— | OH |
| 10 | Asp | —Lys—Glu—Gly—NH(CH$_2$)$_{11}$CO—Asp—Asp—Lys—Lys—Glu—Gly— | OH |
| 11 | Glu | —Asp—Glu—NH(CH$_2$)$_{17}$CO—Lys—Gly—Lys— | OH |
| 12 | —Lys—Glu—Glu—Gly—Asp—Asp—Lys—Lys—Gly—Gly— | —Gly—Lys—Glu—Glu—Asp | OH |
| 13 | Lys | —NH(CH$_2$)$_{17}$CO— | NH$_2$ |
| 14 | —Lys—Lys— | —Asp—Gly— | NH$_2$ |
| 15 | (—Glu—)$_{10}$ | Lys | NH$_2$ |
| 16 | —NH(CH$_2$)$_{11}$CO— | —NH(CH$_2$)$_{11}$CO— | NH$_2$ |

(Note) Two systeinyl mercapto groups in the Cys—Cys moiety in the formula (I) are interlinked to each other to form a disulfide bond.

TABLE 3

| | Example 2 | Example 3 | Example 4 | Example 5 | Example 6 | Example 7 | Example 8 |
|---|---|---|---|---|---|---|---|
| Molecular weight determined by FAB mass spectrometry | 2303 (2302.52) | 2527 (2526.93) | 3088 (3088.343) | 3462 (3461.77) | 3656 (3656.30) | 2716 (2715.95) | 3071 (3071.447) |
| Amino acid composition analyses | | | | | | | |
| Glycine | 1.92 (2) | 0.92 (1) | 0.94 (1) | 0.95 (1) | 0.97 (1) | 6.90 (7) | 1.92 (2) |
| Tryptophane | 2.01 (2) | 2.03 (2) | 2.05 (2) | 2.02 (2) | 2.04 (2) | 2.03 (2) | 2.01 (2) |
| Lysine | 1.03 (1) | 1.05 (1) | 1.06 (1) | 6.18 (6) | 11.21 (11) | 2.08 (2) | 2.03 (2) |
| Histidine | 0.99 (1) | 0.97 (1) | 0.96 (1) | 0.97 (1) | 0.97 (1) | 0.95 (1) | 0.99 (1) |
| Valine | 0.94 (1) | 0.96 (1) | 0.97 (1) | 0.95 (1) | 0.97 (1) | 0.96 (1) | 0.95 (1) |
| Thyrosine | 3.10 (3) | 3.14 (3) | 3.14 (3) | 3.10 (3) | 3.09 (3) | 3.12 (3) | 3.10 (3) |
| Threonine | 2.06 (2) | 2.04 (2) | 2.05 (2) | 2.03 (2) | 2.04 (2) | 2.04 (2) | 2.06 (2) |
| Cystine | 0.87 (1) | 0.86 (1) | 0.84 (1) | 0.85 (1) | 0.87 (1) | 0.85 (1) | 0.86 (1) |
| Proline | 2.09 (2) | 2.06 (2) | 2.05 (2) | 2.07 (2) | 2.09 (2) | 2.08 (2) | 2.09 (2) |
| Aspartic acid | 2.14 (2) | 2.10 (2) | 2.12 (2) | 7.35 (7) | 2.10 (2) | 2.12 (2) | 4.13 (4) |
| Leucine | 0.99 (1) | 1.01 (1) | 1.00 (1) | 1.01 (1) | 1.00 (1) | 0.98 (1) | 0.99 (1) |
| Glutamic acid | — | — | 5.15 (5) | — | 1.02 (1) | — | 1.01 (1) |
| H$_2$N(CH$_2$)$_{11}$COOH | — | — | 0.96 (1) | — | — | — | — |
| H$_2$N(CH$_2$)$_{17}$COOH | — | 0.94 (1) | — | — | — | — | 0.95 (1) |

| | Example 9 | Example 10 | Example 11 | Example 12 | Example 13 | Example 14 | Example 15 | Example 16 |
|---|---|---|---|---|---|---|---|---|
| Molecular weight determined by FAB mass spectrometry | 2559 (2558.863) | 3488 (3487.833) | 3214 (3213.645) | 3920 (3920.145) | 2654 (2654.121) | 2558 (2557.88) | 3664 (3663.80) | 2639 (2639.10) |
| Amino acid composition analyses | | | | | | | | |
| Glycine | 1.94 (2) | 2.91 (3) | 1.98 (2) | 4.92 (5) | 0.96 (1) | 1.93 (2) | 0.96 (1) | 0.95 (1) |
| Tryptophane | 2.02 (2) | 2.02 (2) | 2.03 (2) | 2.01 (2) | 2.02 (2) | 2.02 (2) | 2.01 (2) | 2.03 (2) |
| Lysine | 3.05 (3) | 5.10 (5) | 3.06 (3) | 5.12 (5) | 2.04 (2) | 3.09 (3) | 2.06 (2) | 1.03 (1) |
| Histidine | 0.98 (1) | 0.98 (1) | 0.99 (1) | 0.97 (1) | 0.99 (1) | 0.96 (1) | 0.98 (1) | 0.99 (1) |
| Valine | 0.96 (1) | 0.95 (1) | 0.96 (1) | 0.94 (1) | 0.95 (1) | 0.95 (1) | 0.95 (1) | 0.94 (1) |
| Thyrosine | 3.11 (3) | 3.10 (3) | 3.09 (3) | 3.07 (3) | 3.07 (3) | 3.10 (3) | 3.08 (3) | 3.11 (3) |
| Threonine | 2.05 (2) | 2.04 (2) | 2.05 (2) | 2.06 (2) | 2.05 (2) | 2.06 (2) | 2.05 (2) | 2.07 (2) |
| Cystine | 0.87 (1) | 0.90 (1) | 0.88 (1) | 0.89 (1) | 0.87 (1) | 0.86 (1) | 0.85 (1) | 0.87 (1) |
| Proline | 2.10 (2) | 2.08 (2) | 2.09 (2) | 2.08 (2) | 2.07 (2) | 2.10 (2) | 2.07 (2) | 2.09 (2) |
| Aspartic acid | 2.11 (2) | 5.25 (5) | 3.09 (3) | 5.18 (5) | 2.12 (2) | 3.15 (3) | 2.15 (2) | 2.14 (2) |
| Leucine | 1.00 (1) | 0.98 (1) | 0.99 (1) | 1.00 (1) | 0.99 (1) | 0.99 (1) | 1.01 (1) | 1.00 (1) |
| Glutamic acid | — | 2.04 (2) | 2.03 (2) | 4.07 (4) | — | — | 10.50 (10) | — |
| H$_2$N(CH$_2$)$_{11}$COOH | — | 0.94 (1) | — | — | — | — | — | 1.94 (2) |
| H$_2$N(CH$_2$)$_{17}$COOH | — | — | 0.95 (1) | — | 0.94 (1) | — | — | — |

(Note) The parenthesized numerals indicate theoretical values.

REFERENTIAL EXAMPLES 1 AND 2

A peptide represented by the formula,

H—Gly—Trp—Lys—His—Trp—Val—Tyr—Tyr—Thr—Cys—Cys—Pro—Asp—Thr—Pro—Tyr—Leu—Asp—OH, (Referential Example 1) and a peptide represented by the formula, H—Leu—Leu—Gly—Trp—Lys—His—Trp—Val—

-continued

—Tyr—Tyr—Thr—Cys — Cys—Pro—Asp—Thr—
            |_____|

—Pro—Tyr—Leu—Asp—OH, (Referential Example 2) were obtained by carrying out solid-phase synthesis and purification of peptide in the same manner as in Example 1. As a solid-phase resin, a particulate resin of a styrene-divinylbenzene copolymer (molar ratio of styrene to divinylbenzene 99:1) possessing a 4-[N-(t-butoxycarbonyl)-O$^4$-benzyl-α-Laspartyloxymethyl]phenylacetoamidomethyl group in a ratio of 0.78 m.mol/g (resin) [produced by Applied Biosystems Inc., U.S.A. and marketed under the tradename "PAM Aspartic Acid,t-Boc-L-Asp(OBzl)"]was used.

By analyzing reverse-phase high-speed liquid chromatography, the purified peptides consequently obtained each showed a single peak. The molecular weights of the purified peptides determined by FAB mass spectrometry and the amino acid composition analyses of the products obtained by hydrolyzing the purified peptides with hydrochloric acid were as shown in Table 4.

TABLE 4

|  | Referential Example 1 | Referential Example 2 |
|---|---|---|
| Molecular weight determined by FAB mass spectrometry | 2245 (2245.467) | 2472 (2471.78) |
| Amino acid composition analyses |  |  |
| Glycine | 0.96 (1) | 0.97 (1) |
| Tryptophane | 2.02 (2) | 2.01 (2) |
| Lysine | 1.02 (1) | 1.02 (1) |
| Histidine | 0.97 (1) | 0.98 (1) |
| Valine | 0.95 (1) | 0.94 (1) |
| Thyrosine | 3.12 (3) | 3.11 (3) |
| Threonine | 2.07 (2) | 2.06 (2) |
| Cystine | 0.86 (1) | 0.87 (1) |
| Proline | 2.08 (2) | 2.07 (2) |
| Aspartic acid | 2.12 (2) | 2.15 (2) |
| Leucine | 0.99 (1) | 2.98 (3) |

(Note)
The parenthesized numerals indicate theoretical values.

REFERENTIAL EXAMPLE 3

(a) In 50 ml of dioxane obtained by distillation in the presence of sodium metal, 10 g of cellulose particles (marketed by Seikagaku Kogyo Co., Ltd. under the tradename "CM-Cellulofine CH") were suspended. In the suspension, 0.5 g of N-hydroxysuccinimide and 1.0 g of dicyclohexylcarbodiimide added thereto were shaken overnight at room temperature. The resultant mixture was washed with a phosphate buffer solution (0.02 mol/liter) of pH 7.4 and suction filtered. The particles consequently obtained and 20 ml of a phosphate buffer solution (0.02 mol/liter) of pH 7.4 containing 20 mg of the peptide of Example 1 added thereto were stirred overnight at a temperature of 4° C. The mixture consequently obtained was suction filtered. By analyzing reverse-phase high-speed liquid chromatography, the filtrate was found to contain no unaltered peptide (immobilization ratio of peptide on carrier: about 100%). Thus, about 10 g of cellulose particles having immobilized thereon 20 mg of the peptide of Example 1 were obtained.

(b) In 5-ml aliquots of a phosphate buffer solution (0.02 mol/liter) of pH 7.4 containing sodium chloride in a concentration of 0.15 mol/liter, the peptide-immobilized cellulose particles obtained as described above were suspended in a unit amount of 1 g. The resultant solution were heat treated at various temperatures, i.e. 80° C. (over a water bath under normal atmospheric pressure), 100° C. (over a water bath under normal atmospheric pressure), 121° C. (in an autoclave under application of pressure), and 150° C. (in an autoclave under application of pressure), for 20 minutes. Thus, heat-treated adsorbents were obtained.

REFERENTIAL EXAMPLE 4

(a) About 10 g of polyvinyl alcohol particles having immobilized thereon 18.4 mg of the peptide obtained in Example 2 (ratio of peptide immobilization: about 92%) were obtained by following the procedure of Referential Example 3(a), except that 10 g of polyvinyl alcohol particles (produced by Toso K.K. and marketed under the tradename "CM-Toyopearl 650C") were used in place of 10 g of the cellulose particles and 20 mg of the peptide obtained in Example 2 was used in place of 20 g of the peptide obtained in Example 1.

(b) In 5 ml of a phosphate buffer solution (0.02 mol/liter) of pH 7.4 containing sodium chloride in a concentration of 0.15 mol/liter, 1 g of the peptide-immobilized polyvinyl alcohol particles obtained as described above were suspended. The resultant suspension was heat treated in an autoclave under application of pressure at a temperature of 120° C. for 20 minutes. Thus, a heat-treated adsorbent was obtained.

REFERENTIAL EXAMPLE 5

(a) In 100 ml of toluene solution containing 5 ml of γ-aminopropyl triethoxy silane, 10 g of porous glass particles (produced by Electro-nucleonics Corp., U.S.A. and marketed as "CPG-10-1000") were reacted under reflux for 24 hours. The resultant mixture was washed with dioxane obtained by distillation in the presence of sodium metal and the washed mixture was suction filtered. The particles consequently obtained were suspended in 100 ml of dioxane obtained by distillation in the presence of sodium metal. The resultant suspension and 3 g of succinic anhydride added thereto were stirred overnight at normal room temperature. The resultant mixture was washed with dioxane obtained by distillation in the presence of sodium metal and the washed mixture was suction filtered. The particles consequently obtained were suspended in 50 ml of dioxane obtained by distillation in the presence of sodium metal. The resultant suspension and 0.5 g of N-hydroxysuccinimide and 1.0 g of dicyclohexyl-carbodiimide added thereto were stirred overnight at normal room temperature. The resultant mixture was washed with a phosphate buffer solution (0.02 mol/liter) of pH 7.4 and the washed mixture was suction filtered. The particles consequently obtained and 20 ml of a phosphate buffer solution (0.02 mol/liter) of pH 7.4 containing 20 mg of the peptide of Example 3 added thereto were stirred overnight at a temperature of 4° C. The resultant mixture was suction filtered. As a result, about 10 g of porous glass particles having immobilized thereon 20 mg of the peptide of Example 3 were obtained (ratio of peptide immobilization: about 100%).

(b) A heat-treated adsorbent was obtained by following the procedure of Referential Example 4 (b), except that 1 g of the peptide-immobilized porous glass particles obtained as described above were used in place of 1 g of the polyvinyl alcohol particles having 1 g of peptide immobilized thereon.

REFERENTIAL EXAMPLES 6 TO 18

(a) Peptide-immobilized particulate carriers were obtained by following the procedures of Referential Example 3(a), Referential Example 4(a) and Referential Example 5(a), except that 20 mg of various peptides indicated in Table 5 were used instead. The particulate carriers and the ratios of peptide immobilization on such carriers were as shown in Table 5.

(b) Heat-treated adsorbents were obtained by following the procedure of Referential Example 4(b), except that the peptide-immobilized particulate carriers obtained as described above were used each in a unit amount of 1 g in place of 1 g of the peptide-immobilized polyvinyl alcohol particles obtained in Referential Example 4(a).

TABLE 5

| Referential Example | Peptide | Particulate carrier (Note) | Ratio of immobilization (%) |
|---|---|---|---|
| 6 | Product of Example 4 | Cellulose | About 100 |
| 7 | Product of Example 5 | Cellulose | About 98 |
| 8 | Product of Example 6 | Cellulose | About 100 |
| 9 | Product of Example 7 | Polyvinyl alcohol | About 95 |
| 10 | Product of Example 8 | Polyvinyl alcohol | About 95 |
| 11 | Product of Example 9 | Cellulose | About 95 |
| 12 | Product of Example 10 | Cellulose | About 98 |
| 13 | Product of Example 11 | Cellulose | About 100 |
| 14 | Product of Example 12 | Cellulose | About 100 |
| 15 | Product of Example 13 | Polyvinyl alcohol | About 90 |
| 16 | Product of Example 14 | Polyvinyl alcohol | About 100 |
| 17 | Product of Example 15 | Porous glass | About 95 |
| 18 | Product of Example 16 | Porous glass | About 100 |

(Note)
Cellulose particles: Marketed by Seikagaku Kogyo Co., Ltd. under the tradename "CM-Cellulofine CH"
Polyvinyl alcohol particles: Produced by Toso K.K. and marketed under the tradename "CM-Toyopearl 650C"
Porous glass particles: Produced by Electro-nucleonics Corp., U.S.A. and marketed as "CPG-10-1000"

REFERENTIAL EXAMPLE 19

(a) About 10 g of cellulose particles having immobilized thereon 14.4 mg of the peptide obtained in Referential Example 1 (ratio of peptide immobilization: about 72%) were obtained by following the procedure of Referential Example 3(a), except that 20 mg of the peptide obtained in Referential Example 1 was used in place of 20 mg of the peptide obtained in Example 1.

(b) A heat-treated adsorbent was obtained by following the procedure of Referential Example 4(b), except that 1 g of the peptide-immobilized cellulose particles obtained as described above were used in place of 1 g of the peptide-immobilized polyvinyl alcohol particles.

REFERENTIAL EXAMPLE 20

(a) The immobilization procedure of Referential Example 4(a) was repeated, except that 20 mg of the peptide obtained in Referential Example 2 was used in place of 20 mg of the peptide obtained in Example 2. Since the peptide obtained in Referential Example 2 showed low solubility in the phosphate buffer solution, the unaltered peptide remaining in the filtrate could not be determined by analyzing reverse-phase high-speed liquid chromatography.

(b) A heat-treated adsorbent was obtained by following the procedure of Referential Example 4(b), except that 1 g of the polyvinyl alcohol particles obtained by the immobilization treatment described above were used in place of 1 g of the peptide-immobilized polyvinyl alcohol particles obtained in Referential Example 4(a).

TEST EXAMPLE 1

In 0.5 ml of serum from a patient of myasthenia gravis, 50 mg of the adsorbent obtained in Referential Example 3(a) (cellulose particles having the peptide immobilized thereon) and not yet subjected to any heat treatment or the adsorbent obtained in Referential Example 3(b) and subjected to a heat treatment was suspended at a temperature of 37° C. for three hours. The resultant suspension was centrifuged to separate a supernatant. The supernatant was tested for the concentration of the human antibody to the nicotinic acetylcholine receptor by the Con A method [Protein, Nucleic Acid and Enzyme, vol. 26, pages 1578–1591 (1981)]. To be specific, the specimen was brought into contact sequentially with the nicotinic acetylcholine receptor and a radioisotope-labelled α-bungartoxin. The treated specimen was passed through a column packed with Sepharose having immobilized thereon concanavalin (Con A). By measuring the radioactivity of the column, the amount of the human antibody which was contained in the specimen and which inhibited the union of the α-bungarotoxin with the nicotinic acetylcholine receptor was determined in terms of toxin binding inhibition activity (ratio of decrease of the radioactivity of the column). The results are shown in Table 6. For comparison, the results obtained for the glycine-immobilized cellulose particles produced by following the procedure of Referential Example 3(a), except that glycine was used in place of the peptide of Example 1, and the results obtained for the adsorbent produced by a heat treatment at 121° C. in the same manner as in Referential Example 3(b), except that the glycine-immobilized cellulose particles were used in place of the peptide-immobilized cellulose particles, are shown in the same table.

TABLE 6

| Substance immobilized on cellulose particles | Temperature of heat treatment (°C.) | Toxine binding inhibition activity (%) |
|---|---|---|
| Peptide obtained in Example 1 | No heat treatment | 38 |
| Peptide obtained in Example 1 | 80 | 30 |
| Peptide obtained in Example 1 | 100 | 28 |
| Peptide obtained in Example 1 | 121 | 26 |
| Peptide obtained in Example 1 | 150 | 27 |
| Glycine | No heat treatment | 44 |
| Glycine | 121 | 45 |

TEST EXAMPLE 2

Suspension of serum was carried out by following the procedure of Test Example 1, except that various heat-treated absorbents obtained in Referential Examples 4 to 18 were used in place of the adsorbents obtained in Referential Example 3, one already subjected to heat treatment and the other subjected to no treatment. The supernatant consequently obtained was tested for the concentration of the human antibody to the nicotinic acetylcholine receptor. The results are shown in Table 7. For comparison, the results obtained for the heat-treated adsorbents of Referential Example 19 and Referential Example 20, and the results obtained for the adsorbent produced by heat-treating at 121° C. the glycine-immobilized cellulose particles as used for comparison in Test Example 1 are shown in Table 7.

TABLE 7

| Adsorbent | Toxin binding inhibition activity (%) |
| --- | --- |
| Product of Referential Example 4 | 22 |
| Product of Referential Example 5 | 19 |
| Product of Referential Example 6 | 17 |
| Product of Referential Example 7 | 18 |
| Product of Referential Example 8 | 18 |
| Product of Referential Example 9 | 21 |
| Product of Referential Example 10 | 20 |
| Product of Referential Example 11 | 18 |
| Product of Referential Example 12 | 19 |
| Product of Referential Example 13 | 22 |
| Product of Referential Example 14 | 20 |
| Product of Referential Example 15 | 22 |
| Product of Referential Example 16 | 17 |
| Product of Referential Example 17 | 20 |
| Product of Referential Example 18 | 18 |
| Product of Referential Example 19 | 28 |
| Product of Referential Example 20 | 36 |
| Product obtained by heat-treating glycine-immobilized cellulose particles at 121° C. | 34 |

As demonstrated in the working examples cited above, this invention provides a novel peptide useful for efficient production of an adsorbent capable of effectively adsorbing the human antibody to the nicotinic acetylcholine receptor.

What is claimed is:

1. A peptide represented by the formula:

H-X-Gly-Trp-Lys-His-Trp-Val-Tyr-Tyr-Thr-Cys-Cys-Pro-Asp-Thr-Pro-Tyr-Leu-Asp-Y-Z wherein one of X and Y stands for a single bond, an amino acid residue selected from the class consisting of Asp, Glu, Lys and a divalent group represented by the formula, $$-NH(CH_2)_n\underset{\overset{\|}{O}}{C}-$$

(wherein n stands for an integer in the range of 1 to 17), or a peptide residue formed by peptide linkage of two to ten amino acid residues of at least one species selected from the class mentioned above and the other of X and Y stands for an amino acid residue selected from the class consisting of Asp, Glu, Lys and a divalent group represented by the formula, $$-NH(CH_2)_n\underset{\overset{\|}{O}}{C}-$$

(wherein n stands for an integer in the range of 1 to 17), or a peptide residue formed by peptide linkage of two to ten amino acid residues of at least one species selected from the class mentioned above, and Z stands for one member selected from the class consisting of hydroxyl group and amino group.

2. A peptide according to claim 1, wherein two cysteinyl mercapto groups in the Cys-Cys moiety of the amino acid sequence are interlinked to each other to form a disulfide bond.

3. A peptide according to claim 1, wherein the peptide residue is one member selected from the group consisting of $-Asp-Asp-$, $-Glu-Glu-$, $-Lys-Lys-$, $-Gly-Gly-$, $(NH(CH_2)_{11}\underset{\overset{\|}{O}}{C})_2$, $(NH(CH_2)_{17}\underset{\overset{\|}{O}}{C})_2$, $-Asp-Glu-$, $-Asp-Gly-$, $-Gly-Asp-$, $-Glu-Lys-$, $-Lys-Glu-$, $-Lys-NH(CH_2)_{11}\underset{\overset{\|}{O}}{C}-$, $-Gly-Asp-$, $-Gly-Lys-$, $-NH(CH_2)_{11}\underset{\overset{\|}{O}}{C}-Glu-$, $-NH(CH_2)_{11}\underset{\overset{\|}{O}}{C}-Lys-$, $-NH(CH_2)_{17}\underset{\overset{\|}{O}}{C}-Asp-$, $-NH(CH_2)_{17}\underset{\overset{\|}{O}}{C}-Lys-$, $-Lys-Lys-Gly-$, $(Asp)_5$, $(Glu)_5$, $(Lys)_5$, $(Gly)_5$, $(NH(CH_2)_{11}\underset{\overset{\|}{O}}{C})_5$, $(NH(CH_2)_{17}\underset{\overset{\|}{O}}{C})_5$, $-Lys-Asp-Glu-Gly-NH(CH_2)_{17}\underset{\overset{\|}{O}}{C}-$, $-Gly-Lys-Glu-Glu-Asp-$, $-Asp-Glu-NH(CH_2)_{17}\underset{\overset{\|}{O}}{C}-Lys-Gly-Lys-$, $(Asp)_{10}$, $(Glu)_{10}$, $(Lys)_{10}$, $(Gly)_{10}$, $(NH(CH_2)_{11}\underset{\overset{\|}{O}}{C})_{10}$, $(NH(CH_2)_{17}\underset{\overset{\|}{O}}{C})_{10}$, $-Lys-Glu-Gly-NH(CH_2)_{11}\underset{\overset{\|}{O}}{C}-Asp-Asp-Lys-$ $-Lys-Glu-Gly-$, and $-Lys-Glu-Glu-Gly-$ $-Asp-Asp-Lys-Lys-Gly-Gly-$.

* * * * *

UNITED STATES PATENT AND TRADEMARK OFFICE
CERTIFICATE OF CORRECTION

PATENT NO. : 4,889,917

DATED : 12/26/89

INVENTOR(S) : Masao Tanihara, et al

It is certified that error appears in the above-identified patent and that said Letters Patent is hereby corrected as shown below:

On the title page:

--Assignee is incorrectly recorded. It should read: Agency of Industrial Science & Technology, Ministry of International Trade & Industry--

Signed and Sealed this

Twenty-sixth Day of March, 1991

Attest:

HARRY F. MANBECK, JR.

Attesting Officer

Commissioner of Patents and Trademarks